(12) United States Patent
Racz et al.

(10) Patent No.: US 8,500,715 B2
(45) Date of Patent: *Aug. 6, 2013

(54) CATHETER CONNECTION HUB

(75) Inventors: N. Sandor Racz, Coppell, TX (US); Gary Bullard, Saratoga Springs, NY (US)

(73) Assignee: Custom Medical Applications, Inc., Johnston, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/317,330

(22) Filed: Oct. 14, 2011

(65) Prior Publication Data

US 2012/0041423 A1 Feb. 16, 2012

Related U.S. Application Data

(63) Continuation of application No. 11/886,100, filed as application No. PCT/US2006/008917 on Mar. 10, 2006, now Pat. No. 8,038,667.

(60) Provisional application No. 60/660,222, filed on Mar. 10, 2005.

(51) Int. Cl.
*A61M 25/16* (2006.01)
*A61M 25/18* (2006.01)
*A61M 5/178* (2006.01)

(52) U.S. Cl.
USPC ............... 604/533; 604/535; 604/167.02

(58) Field of Classification Search
USPC ... 604/19, 48, 93.01, 164.01, 167.01–167.06, 604/533–539
See application file for complete search history.

(56) References Cited

U.S. PATENT DOCUMENTS 3,920,215 A 11/1975 Knauf
4,327,723 A 5/1982 Frankhouser
(Continued)

FOREIGN PATENT DOCUMENTS

EP 0 856 332 8/1998
EP 1 033 146 9/2000
(Continued)

OTHER PUBLICATIONS

PCT International Preliminary Report on Patentability, dated Sep. 12, 2007 containing PCT Written Opinion of the International Searching Authority, dated Sep. 5, 2006.

(Continued)

*Primary Examiner* — Matthew F Desanto
(74) *Attorney, Agent, or Firm* — TraskBritt

(57) ABSTRACT

Fluid communication to an end of a catheter is afforded through a connection hub selectively attachable thereto. The connection hub includes a catheter receiving element and a fluid coupling element that are relatively rotatable coaxially between a catheter receiving condition and a catheter capture condition of the connection hub. The catheter capture condition, a compressible sealing sleeve disposed interior of the connection hub between a pair of clamping jaws projecting from the catheter receiving element is urged into sealing engagement with the exterior of the catheter, catheter is gripped mechanically through the sealing sleeve by the clamping jaws. The exteriors of each of the catheter receiving element and the fluid coupling element are formed into planar actuation handles that facilitate relative rotation of the catheter receiving element and the fluid coupling element into coplanar alignment in the catheter capture condition of the connection hub.

19 Claims, 11 Drawing Sheets

U.S. PATENT DOCUMENTS

| | | | |
|---|---|---|---|
| 4,378,013 A | 3/1983 | LeFevre | |
| 4,613,329 A * | 9/1986 | Bodicky | 604/158 |
| 4,834,719 A | 5/1989 | Arenas | |
| 4,842,592 A | 6/1989 | Caggiani et al. | |
| 4,895,570 A | 1/1990 | Larkin | |
| 4,929,236 A | 5/1990 | Sampson | |
| 5,127,626 A | 7/1992 | Hilal et al. | |
| 5,149,324 A | 9/1992 | Clawson | |
| 5,279,597 A | 1/1994 | Dassa et al. | |
| 5,505,714 A | 4/1996 | Dassa et al. | |
| 5,507,733 A | 4/1996 | Larkin et al. | |
| 5,522,803 A | 6/1996 | Teissen-Simony | |
| 5,538,009 A | 7/1996 | Byrne et al. | |
| 5,676,680 A | 10/1997 | Lim | |
| D408,530 S | 4/1999 | Eliasen et al. | |
| 5,968,011 A | 10/1999 | Larsen et al. | |
| 5,993,437 A | 11/1999 | Raoz | |
| 6,086,575 A | 7/2000 | Mejslov | |
| 6,099,519 A | 8/2000 | Olsen et al. | |
| D433,503 S | 11/2000 | Powers et al. | |
| 6,190,372 B1 | 2/2001 | Racz | |
| 6,254,589 B1 | 7/2001 | Raoz | |
| 6,332,874 B1 | 12/2001 | Eliasen et al. | |
| 6,572,586 B1 | 6/2003 | Wojcik | |
| 6,749,589 B1 * | 6/2004 | Douglas et al. | 604/165.01 |
| 6,971,390 B1 | 12/2005 | Vasek et al. | |
| 7,192,433 B2 | 3/2007 | Osypka et al. | |
| 7,303,543 B1 | 12/2007 | Maule et al. | |
| 7,850,658 B2 | 12/2010 | Faust et al. | |
| 8,038,667 B2 * | 10/2011 | Racz et al. | 604/533 |
| 2002/0173769 A1 * | 11/2002 | Gray et al. | 604/506 |
| 2004/0054336 A1 | 3/2004 | Klint et al. | |

FOREIGN PATENT DOCUMENTS

| | | |
|---|---|---|
| WO | WO 03/030985 | 4/2003 |
| WO | 2004/018015 | 3/2004 |
| WO | 2006/099306 | 9/2006 |

OTHER PUBLICATIONS

PCT International Search Report and Written Opinion dated Sep. 5, 2006.

Prior art search from Korean Intellectual Property Rights Information Service dated Apr. 4, 2011.

* cited by examiner

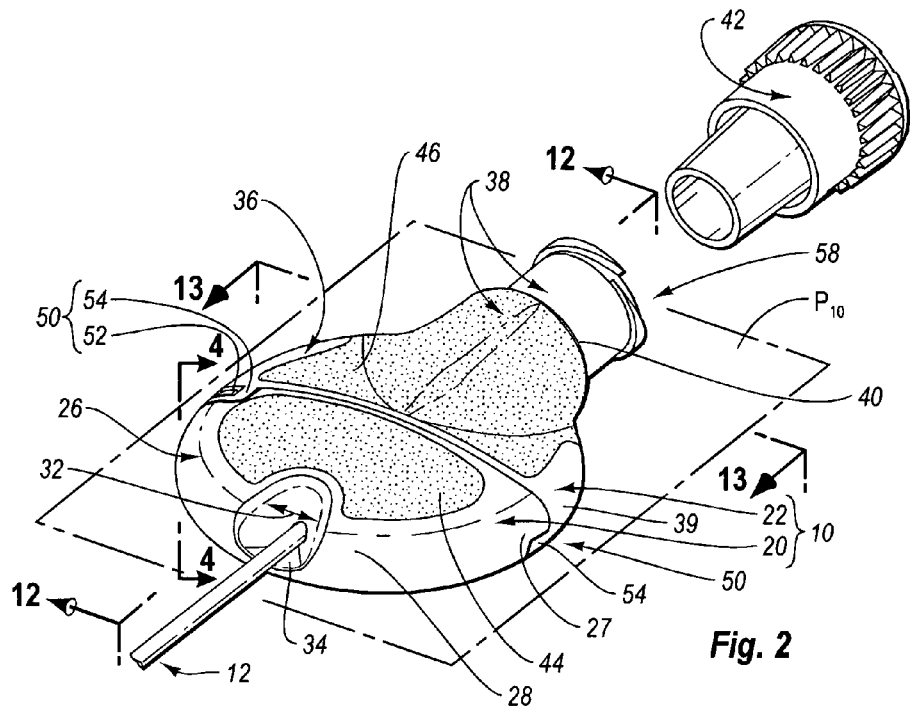
Fig. 2
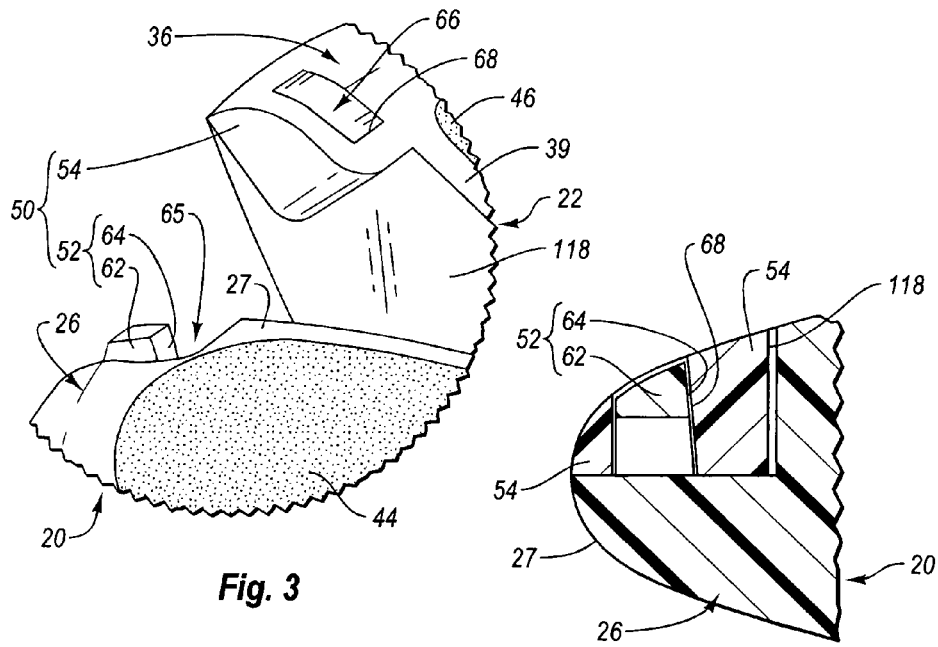
Fig. 3
Fig. 4

CATHETER CONNECTION HUB

CROSS-REFERENCE TO RELATED APPLICATIONS

This application is a continuation of U.S. patent application Ser. No. 11/886,100, filed Oct. 12, 2007, now U.S. Pat. No. 8,038,667 (Oct. 18, 2011), and is a national phase entry under 35 U.S.C. §371 of International Patent Application PCT/US2006/008917, filed Mar. 10, 2006, published in English as International Patent Publication WO 2006/099306 A2 on Sep. 21, 2006, which claims the benefit under Article 8 of the Patent Cooperation Treaty to U.S. Provisional Patent Application No. 60/660,222, filed Mar. 10, 2005, and titled "Catheter Connection Hub," the entire disclosure of each of which is hereby incorporated herein by this reference.

TECHNICAL FIELD

Generally, various embodiments of the invention relate to medical devices and to connection hubs attachable to a free end of a catheter to enable selective fluid communication with the interior of that catheter. More particularly, the invention relates to such connection hubs as are attachable in the field at the time of use through manual manipulation by medical personnel.

BRIEF DESCRIPTION OF THE DRAWINGS

The principles of the invention will be understood by a more particular description of illustrative embodiments in accordance with the invention rendered by reference to specific illustrative embodiments thereof that are illustrated in the appended drawings. Understanding that these drawings depict only illustrative embodiments of the invention and are not, therefore, to be considered limiting of its scope, the invention will be described and explained with additional specificity and detail through the use of the accompanying drawings in which:

FIG. 2 is a perspective view of the connection hub of FIG. 1 in the catheter capture condition thereof attached to the free end of the catheter of FIG. 1;

FIG. 3 is an enlarged fragmentary perspective view of the structures of the connection hub of FIG. 1 that latch the elements of the connection hub of FIGS. 1 and 2 in the catheter capture condition thereof shown in FIG. 2;

FIG. 4 is a transverse cross section of the connection hub of FIG. 2 taken along section line 4-4 therein, thereby depicting the structures illustrated in FIG. 3 interacting to latch the elements of the connection hub of FIGS. 1 and 2 in the catheter capture condition thereof shown in FIG. 2;

DETAILED DESCRIPTION

Figure 1:
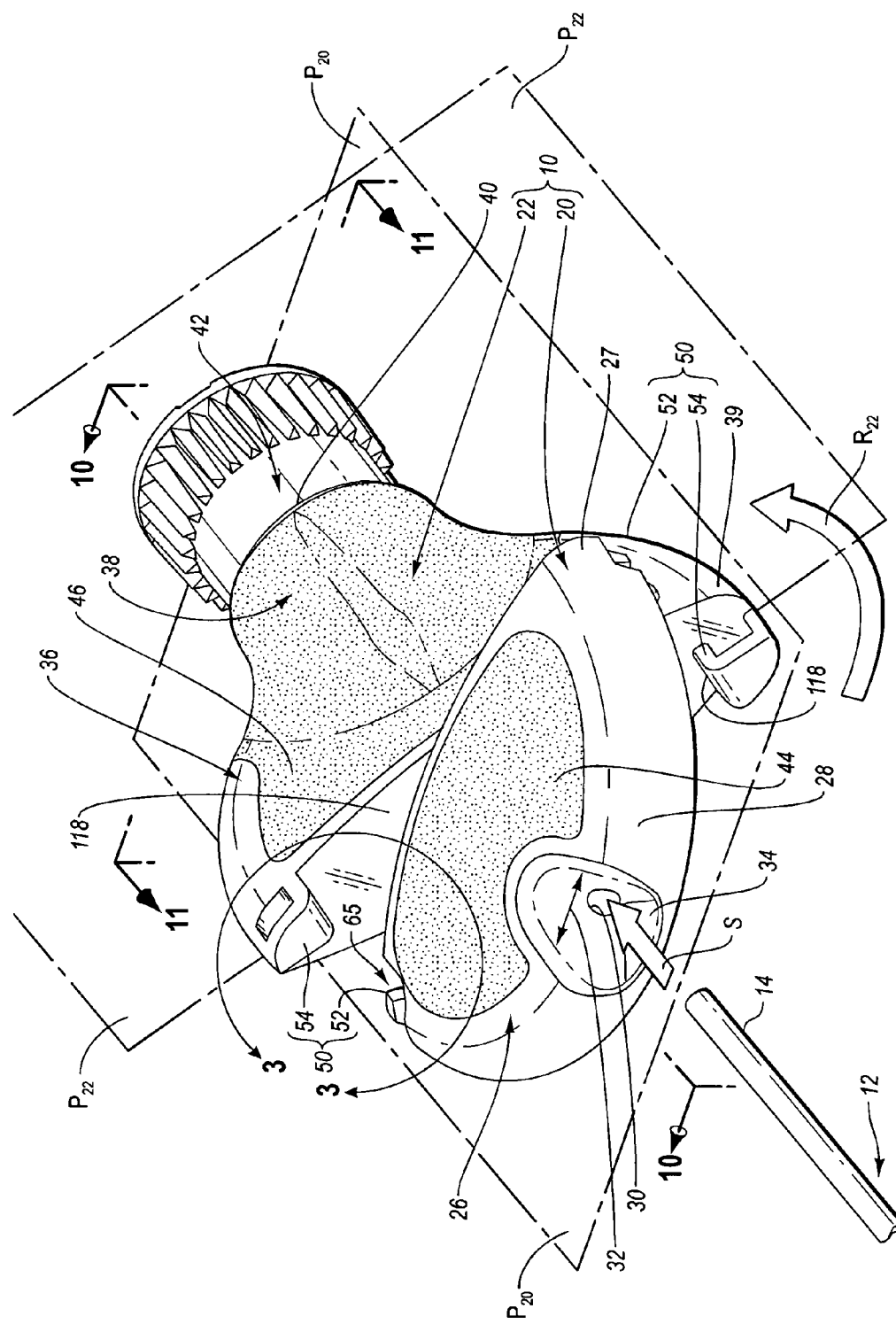
FIG. 1 is a perspective view of a connection hub embodying teachings of the present invention shown in the catheter receiving condition thereof about to admit into the connection hub the free end of a catheter to be attached thereto.

By way of overview, FIG. 1 presents a connection hub 10 embodying teachings of the present invention and a catheter 12, the free end 14 of which is to be attached thereto for the purpose of enabling selective fluid communication to be effected with the interior of catheter 12 from free end 14 thereof The components of connection hub 10 apparent from the exterior view thereof presented in FIG. 1 include a catheter receiving element 20 and a fluid coupling element 22 that are secured in an abutting relationship so as to be capable of engaging in coaxial rotation relative to each other. Such relative rotation $R_{22}$ is indicated by an arrow in FIG. 1 that is oriented in the direction in which fluid coupling element 22 is to be rotated relative to catheter receiving element 20 in order to attach connection hub 10 to catheter 12 once catheter 12 has been entered into connection hub 10 in the manner suggested by arrow S also shown in FIG. 1.

Interior structures of connection hub 10 that are not visible in FIG. 1 actually effect the rotational interconnection of catheter receiving element 20 and fluid coupling element 22. Other interior structures serve to attach connection hub 10 to catheter 12 by mechanically gripping free end 14 of catheter 12 and by establishing a fluid seal about the exterior thereof.

Nonetheless, the portion of catheter receiving element 20 visible in FIG. 1 takes the form of an actuation handle 26 for catheter receiving element 20. Actuation handle 26 has a generally planar external appearance that defines a plane $P_{20}$ of catheter receiving element 20. In the embodiment depicted, actuation handle 26 is a flattened semicircular disk, although alternative planar shapes in such an actuation handle would be consistent with the teachings of the present invention. Actuation handle 26 has an abutment end 27 adjacent to fluid coupling element 22 and an outer end 28 remote therefrom that is configured to slidably admit free end 14 of catheter 12 into connection hub 10. The entry of free end 14 of catheter 12 into connection hub 10 occurs by way of an access opening 30 located at the narrowed terminus of a funnel-shaped, open-topped guideway 32 recessed into outer end 28 of actuation handle 26 on the side thereof visible in FIG. 1. Guideway 32 thus has a wedge-shaped floor 34 that is parallel to plane $P_{20}$ of catheter receiving element 20. This configuration in guideway 32 enables medical personnel to enter free end 14 of catheter 12 into connection hub 10 without having to view access opening 30 within plane $P_{20}$ of catheter receiving element 20.

The portion of fluid coupling element 22 visible in FIG. 1 takes the form of an actuation handle 36 for fluid coupling element 22. Actuation handle 36 has a generally planar external appearance that defines a plane $P_{22}$ of fluid coupling element 22. In the embodiment depicted, actuation handle 36 is a flattened semicircular disk, although alternative planar shapes in such an actuation handle would be consistent with the teachings of the present invention. Fluid coupling element 22 has an abutment end 39 adjacent to catheter receiving element 20 and remotely therefrom an outer end 40 configured to effect selective fluid communication through connection hub 10 with the free end of any catheter to which connection hub 10 becomes attached. Toward that end, fluid coupling element 22 is provided at outer end 40 with a neck 38 that extends radially outwardly from actuation handle 36. The free end of neck 38 is designed to allow selective fluid communication to be effected through connection hub 10 with the free end of any catheter attached thereto. In FIG. 1, however, the free end of neck 38 is obscured by a cap 42 that has been threaded onto the free end of neck 38 to preclude such fluid communication.

In FIG. 1, plane $P_{22}$ of fluid coupling element 22 is in a noncoplanar relationship to plane $P_{20}$ of catheter receiving element 20. The degree of the nonalignment between plane $P_{22}$ of fluid coupling element 22 and plane $P_{20}$ of catheter receiving element 20 can, however, be reduced through rotation $R_{22}$ of fluid coupling element 22 relative to catheter receiving element 20 in the direction indicated by the arrow associated with rotation $R_{22}$. Such is the manipulation that occurs in order to actually attach connection hub 10 to the free end of a catheter that has been admitted through access opening 30 into connection hub 10. The planar exterior configuration of catheter receiving element 20 as actuation handle 26 and the planar exterior configuration of fluid coupling element 22 as actuation handle 36 facilitates such relative rotation between catheter receiving element 20 and fluid coupling element 22.

Catheter receiving element 20 and fluid coupling element 22 may be comprised of a relatively hard, moldable plastic, such as ABS, polycarbonate, lexan, polyamide, nylon, PE or an ABS-polycarbonate blend. Such materials are easily formed in known manufacturing processes to produce articles of structurally rigid, but not brittle, constitution. Thin structures made of such materials can as well be made to exhibit desirable degrees of resilient deformability.

The exterior surface of actuation handle 26 of catheter receiving element 20 may be provided with one or more inlay regions 44 having contrasting material properties from those exhibited by the balance of catheter receiving element 20. Similarly, the exterior surface actuation handle 36 of fluid coupling element 22 may be provided with one or more inlay regions 46 made of a material having contrasting properties to those of the material of which the balance of fluid coupling element 22 is comprised. One material of which each of inlay regions 44, 46 may be comprised is a soft, skin-compatible material, such as Krayton, thermoplastic rubber, SAN, TPR, TPU, or Santoprene. The use of such soft materials in areas, such as inlay regions 44, 46, on exterior surfaces of elements of connection hub 10, contributes positively to the purchase made available to medical personnel in manipulating actuation handle 26 of catheter receiving element 20 and actuation handle 36 of fluid coupling element 22 to cause rotation $R_{22}$ of fluid coupling element 22. Inlay regions 44, 46, also contribute to patient comfort when connection hub 10 is rested against the skin.

Abutting end 27 of actuation handle 26 of catheter receiving element 20 and abutting end 39 of actuation handle 36 of fluid coupling element 22 are provided with latches 50 that each include a paired hook 52 and an eye 54 that are located in an opposed relationship on respective of catheter receiving element 20 and fluid coupling element 22. Latches 50 limit the extent of relative rotation possible between fluid coupling element 22 and catheter receiving element 20. Latches 50 engage once rotation $R_{22}$ of fluid coupling element 22 relative to catheter receiving element 20 has caused connection hub 10 to become attached to the free end of a catheter, a condition that will hereinafter be referred to as the catheter capture condition of the elements of connection hub 10. Once engaged, latches 50 thus also preclude the inadvertent dislodgement of fluid coupling element 22 and catheter receiving element 20 out of the catheter capture condition of connection hub 10.

FIG. 2 depicts the catheter capture condition of connection hub 10. There, plane $P_{22}$ of fluid coupling element 22 has been subjected to rotation $R_{22}$ relative to catheter receiving element 20 sufficient to be in a coplanar relationship with plane $P_{20}$ of catheter receiving element 20. Correspondingly, connection hub 10 takes on a generally planar appearance that defines a plane $P_{10}$ of connection hub 10 in the catheter capture condition thereof.

In FIG. 2, cap 42 is shown threaded off of the free end of neck 38 of fluid coupling element 22. Revealed, as a result, on the free end of neck 38 is a standard luer connector 58 by which it is possible to place auxiliary medical equipment in fluid communication with catheter 12 through connection hub 10. In the catheter capture condition of connection hub 10, abutment end 27 of actuation handle 26 of catheter receiving element 20 is in congruent face-to-face engagement with abutment end 39 of actuation handle 36 of fluid coupling element 22. Connection hub 10 takes on the external overall appearance of a circular disk with neck 38 projecting radially therefrom. Catheter receiving element 20 and fluid coupling element 22 are restrained from easy dislodgement from the catheter capture condition of connection hub 10 by the interaction of hooks 52 and eyes 54 of latches 50. A typical set of such structures is depicted with enhanced detail in FIGS. 3 and 4.

FIG. 3 corresponds to the catheter receiving condition of connection hub 10 shown in FIG. 1. Hook 52 comprises a shaft 62 with a barb 64 housed in a recess 65 in the exterior of actuation handle 16 of catheter receiving element 20. Eye 54 on fluid coupling element 22 encloses a capture surface 66 that is provided with a detent 68 complimentary in shape and location in hook 52 to barb 64 on shaft 62. As catheter receiving element 20 and fluid coupling element 22 are rotated toward the catheter capture condition of connection hub 10, hook 52 enters eye 54. Barb 64 bears along capture surface 66, resiliently deforming shaft 62 of hook 52 away from capture surface 66. Once catheter receiving element 20 and fluid coupling element 22 reach a coplanar orientation in the catheter capture condition of connection hub 10, barb 64 reaches detent 68 and snaps resiliently thereinto. This relationship is depicted in cross section in FIG. 4. Latches 50 thus serve as stops to the relative rotation of fluid coupling element 22 and catheter receiving element 20, and latches 50 constrain these elements of connection hub 10 from inadvertent dislodgement out of the catheter capture condition thereof.

Figure 5:
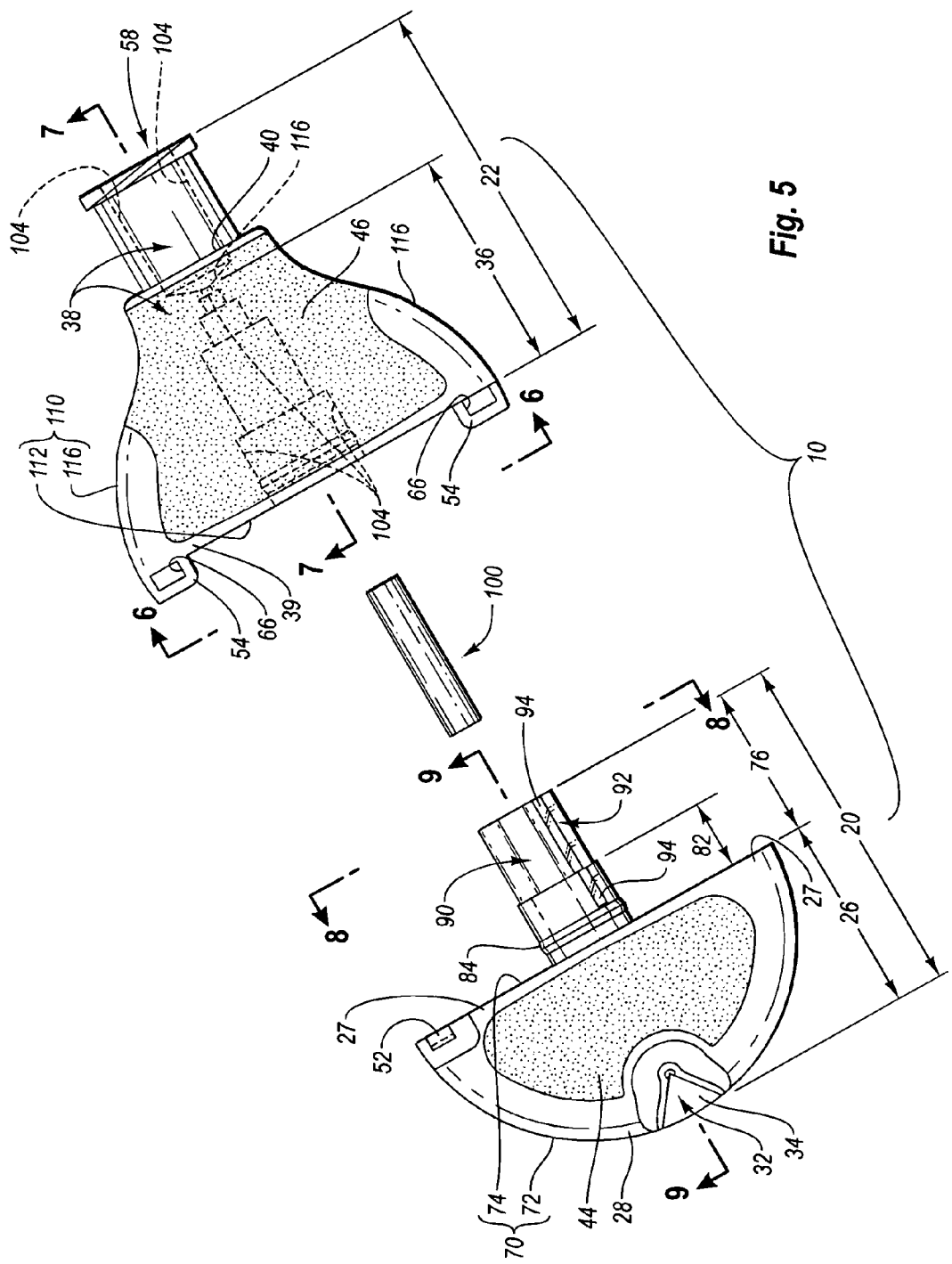
FIG. 5 is an exploded plan view of the connection hub of FIGS. 1 and 2.

FIG. 5 presents an exploded plan view of the elements of connection hub 10 that reveals additional aspects of connection hub 10.

Actuation handle 26 of catheter receiving element 20 is shown in FIG. 5 to have a semicircular outer periphery 70 that includes an arcuate portion 72 that encompasses outer end 28 of actuation handle 26 and a linear diametrical portion 74 at abutment end 27 thereof. Also revealed in FIG. 5 is a columnar structure 76 that projects normal to abutment end 27 of actuation handle 26 from a central location therealong. The base of columnar structure 76 is a cylindrical axle 82 that is circumscribed at a medical position therealong by a continuous, raised retention ridge 84. Axle 82 and retention ridge 84 in cooperation with corresponding structures internal to fluid coupling element 22 secure catheter receiving element 20 and fluid coupling element 22 in the relative rotational relationship that permits the transformation of connection hub 10 of the catheter receiving condition thereof shown in FIG. 1 into the catheter capture condition thereof illustrated in FIG. 2.

Projecting from axle 82 in alignment therewith are a first clamping jaw 90 and a second clamping jaw 92. Clamping jaws 90, 92 are separated by an elongated slot 94 that extends diametrically across columnar structure 76 and longitudinally therethrough into axle 83 to retention ridge 84.

An additional element of connection hub 10 first apparent in FIG. 5 is a tubular sealing sleeve 100. Sealing sleeve 100 may be comprised of synthetic polyisoprene, TPR, TPU, SAN, Santoprene, latex, or rubber. Sealing sleeve 100 is the element of connection hub 10 that interacts most intimately with the free end of a catheter that is attached to connection hub 10. Sealing sleeve 100 is housed between first clamping jaw 90 and second clamping jaw 92, when catheter receiving element 20 and fluid coupling element 22 are assembled as in FIGS. 1 and 2. Under these circumstances, axle 82, clamping jaws 90, 92, and sealing sleeve 100 are entered into an interior space 104 of fluid coupling element 22 that is shown in dashed lines in FIG. 5.

In the plan view presented in FIG. 5, the periphery 110 of actuation handle 36 of fluid coupling element 22 is generally semicircular in shape, including a linear diametrical portion 112 formed at abutment end 39 of fluid coupling element 22 and an arcuate portion 116, as indicated in phantom, interrupted, at outer end 40 of actuation handle 36 of fluid coupling element 22, by neck 38.

Figure 6:
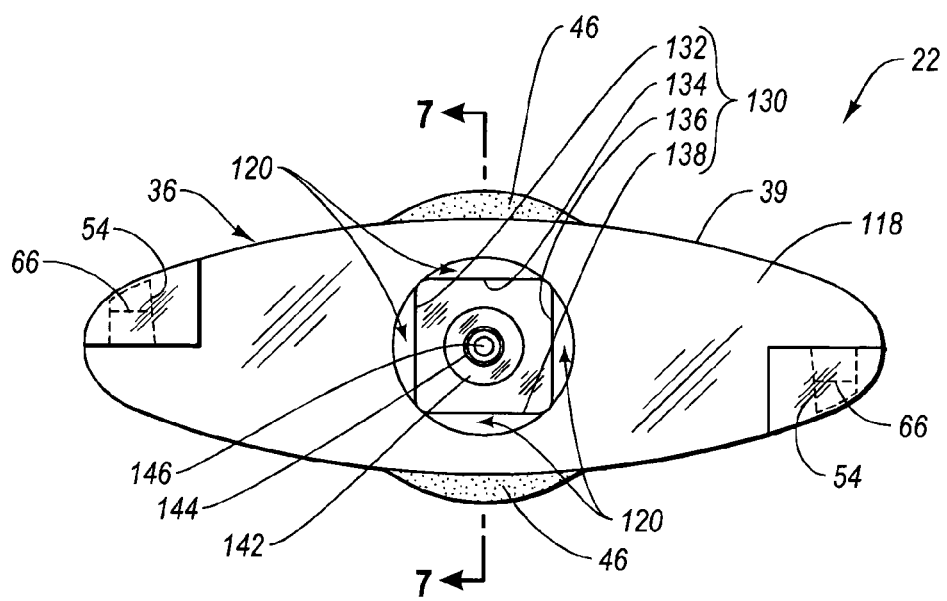
FIG. 6 is an end view of the fluid coupling element of the connection hub of FIG. 5 taken from the perspective of line 6-6 therein.
Figure 7:
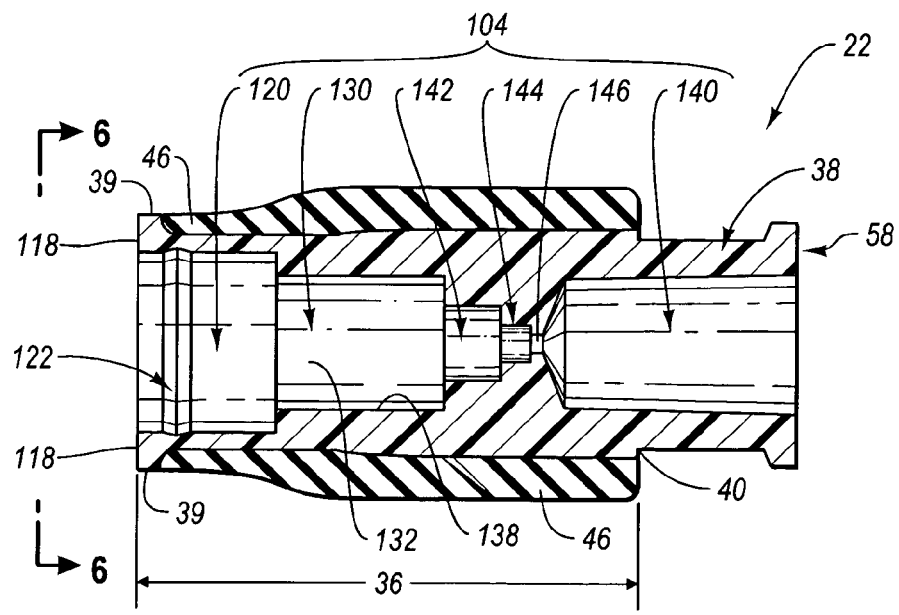
FIG. 7 is a longitudinal cross section of the fluid coupling element shown in FIGS. 5 and 6 taken along section line 7-7 therein.

A better understanding of interior space 104 in fluid coupling element 22 can be acquired by reference to FIGS. 6 and 7 taken together. There, it should first be appreciated that diametrical portion 112 of periphery 110 of actuation handle 36 of fluid coupling element 22 corresponds to a planar interface surface 118 of actuation handle 36 located at abutment end 39 thereof. Opening centrally of interface surface 118 is a cylindrical bore 120 that is encircled by a continuous retention groove 122. Bore 120 and retention groove 122 are so sized as to enable retention ridge 84 on the exterior of axle 82 to be snappingly received into retention groove 122, when catheter receiving element 20 and fluid coupling element 22 are assembled into abutment as shown in FIGS. 1 and 2.

Opening to the exterior of fluid coupling element 22 through bore 120 is a clamp actuation socket 130 that is bounded by perpendicular walls 132, 134, 136, 138, of equal length. Thus, clamp actuation socket 130 is possessed of a transverse cross-sectional shape shown to best advantage in FIG. 6 as being square.

The end of clamp actuation socket 130 opposite from bore 120 communicates through a series of three coaxially disposed spaces of reducing diameter with the interior 140 of luer connector 58. Moving from clamp actuation socket 130 toward interior 140 of luer connector 58, these cylindrical spaces include: first, a sealing sleeve abutment chamber 142; second, a smaller catheter abutment chamber 144; and lastly, a diminutive fluid passageway 146 calculated to afford fluid communication from interior 140 of luer connector 58 to the interior of the free end of any catheter lodged in catheter abutment chamber 144.

Figure 8:
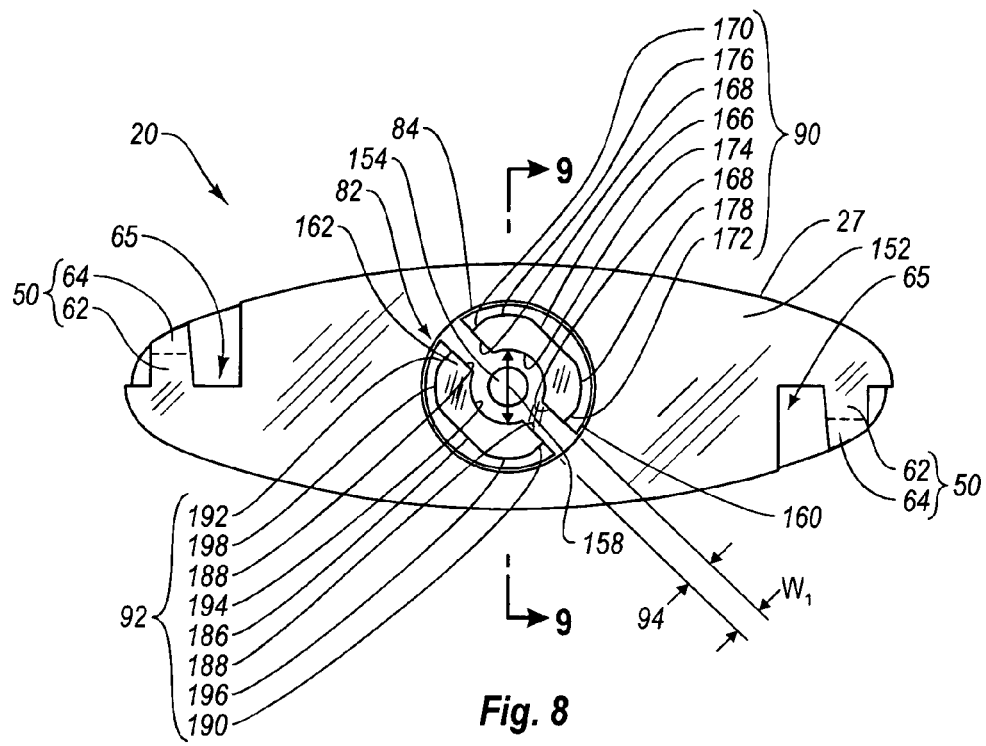
FIG. 8 is an end view of the catheter receiving element of the connection hub of FIG. 5 taken from the perspective of line 8-8 therein.
Figure 9:
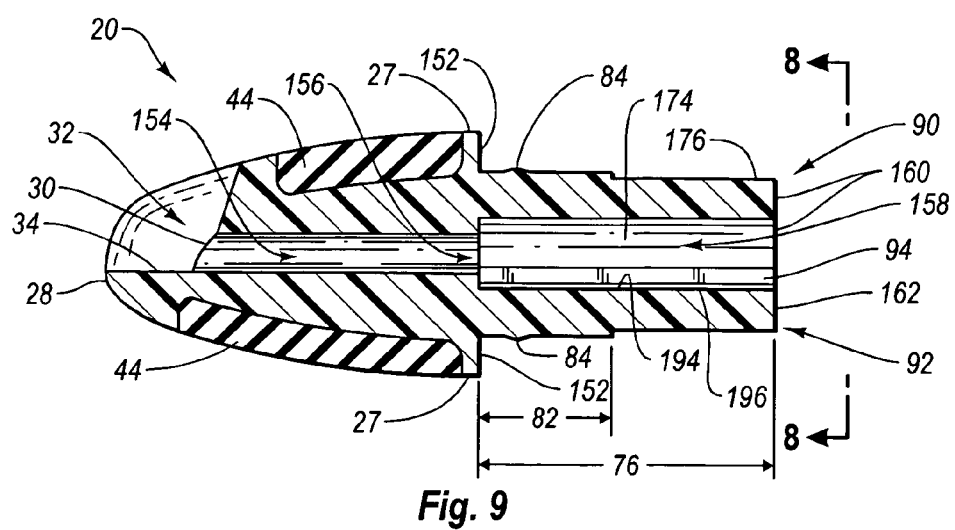
FIG. 9 is a longitudinal cross section of the catheter receiving element of FIGS. 5 and 8 taken along section line 9-9 therein.

An understanding of columnar structure 76 projecting from abutment end 118 of actuation handle 26 can be acquired by reference to FIGS. 8 and 9 taken together. There, it should first be appreciated that diametrical portion 74 of periphery 70 of actuation handle 26 corresponds to a planar interface surface 152 from which columnar structure 76 projects centrally. Formed centrally through actuation handle 26 of catheter receiving element 20 is a catheter passageway 154 that extends from access opening 30 at outer end 28 of actuation handle 26 to an inner opening 156 at abutment end 27 thereof. At inner opening 156, catheter passageway 154 opens into larger sealing sleeve receiving chamber 158 that extends centrally through the full length of columnar structure 76, sharing, in part, space interior of columnar structure 76 identified earlier as comprising slot 94 between clamping jaws 90, 92.

In the assembled condition of connection hub 10 illustrated in FIGS. 1 and 2, the end of sealing sleeve 100 remote from catheter abutment chamber 144 is disposed directly facing inner opening 156 to catheter passageway 154 in actuation handle 26 of catheter receiving element 22. Sealing sleeve 100, receiving chamber 158, and catheter abutment chamber 144 are so sized as to accommodate the full length of sealing sleeve 100 and so oriented mutually as to align the interior passageway in sealing sleeve 100 between catheter passageway 154 in actuation handle 26 and catheter abutment chamber 144 of interior space 104 in fluid coupling element 22.

As a consequence of these relationships in columnar structure 176, clamping jaws 90, 92, can be understood to project from abutment end 27 of actuation handle 26 on opposite sides of inner opening 156 to catheter passageway 154. Clamping jaws 90, 92, terminate at equal distances from abutment end 27 of actuation handle 26. First clamping jaw 90 thus terminates in a first clamp tip 160, and second clamp jaw 92 terminates in a second clamp tip 162.

As appreciated most readily by reference to FIG. 8, first clamping jaw 90 is an elongated, planar structure bounded by a wide, flat outer surface 166 and a parallel, flat inner clamp surface 168. Outer surface 166 and clamp surface 168 are connected at the ends thereof by respective shorter side surfaces 170, 172. Clamp surface 168 of first clamping jaw 90 thus defines one side of slot 94 in columnar structure 76 between clamping jaws 90, 92.

The positioning of sealing sleeve receiving chamber 158 centrally of columnar structure 76 in a space shared with slot 94, in combination with a diameter in sealing sleeve receiving chamber 158 that is larger than the width $W_1$ of slot 94 shown in FIGS. 8 and 9, results in clamp surface 168 of first clamping jaw 90 being traversed centrally by a longitudinally extending, open-ended catheter accommodation recess 174 of semicircular cross section. Catheter accommodation recess 174 is aligned with inner opening 156 to catheter passageway 154 when, as in FIGS. 8 and 9, first clamping jaw 90 is free from the influence of external forces. In the embodiment illustrated, the transverse cross-sectional configuration of first clamping jaw 90 is invariant along the full length thereof Significantly, relative to the action of first clamping jaw 90 in attaching connection hub 10 to the free end of a catheter, outer surface 166 of first clamping jaw 90 and end surface 170 thereof are interconnected in a smooth, tangential manner by a curved bearing surface 176. Similarly, outer surface 166 of first clamping jaw 90 and end surface 172 thereof are interconnected in a smooth, tangential manner by a curved bearing surface 178.

Second clamping jaw 92 is structured identically to first clamping jaw 90. Thus, first clamping jaw 90 is an elongated, planar structure bounded by a wide, flat outer surface 186 and a parallel, flat inner clamp surface 188. Outer surface 186 and clamp surface 188 are connected at the ends thereof by respective shorter side surfaces 190, 192. Inner clamp surface 198 of second clamping jaw 92 thus defines one side of slot 94 in columnar structure 96 between clamping jaws 90, 92.

The positioning of sealing sleeve receiving chamber 158 centrally of columnar structure 76 in a space shared with slot 94, in combination with a diameter in sealing sleeve receiving chamber 158 that is larger than the width $W_1$ of slot 94 shown in FIGS. 8 and 9, results in clamp surface 188 of first clamping jaw 90 being traversed centrally by a longitudinally extending, open-ended catheter accommodation recess 194 of semicircular cross section. Catheter accommodation recess 194 is aligned with inner opening 156 to catheter passageway 174 when, as in FIGS. 8 and 9, second clamping jaw 92 is free from the influence of external forces. In the embodiment illustrated, the transverse cross-sectional configuration of second clamping jaw 92 is invariant along the full length thereof Significantly, relative to the action of second clamping jaw 92 in attaching connection hub 10 to the free end of a catheter, outer surface 186 of second clamping jaw 92 and end surface 190 thereof are interconnected in a smooth, tangential manner by a curved bearing surface 196. Similarly, outer surface 186 of second clamping jaw 92 and end surface 192 thereof are interconnected in a smooth, tangential manner by a curved bearing surface 198. Free end 14 of catheter 12 has been slid through catheter passageway 154 in catheter receiving element 20, through the full length of sealing sleeve 100, and into catheter abutment chamber 144.

Figure 10:
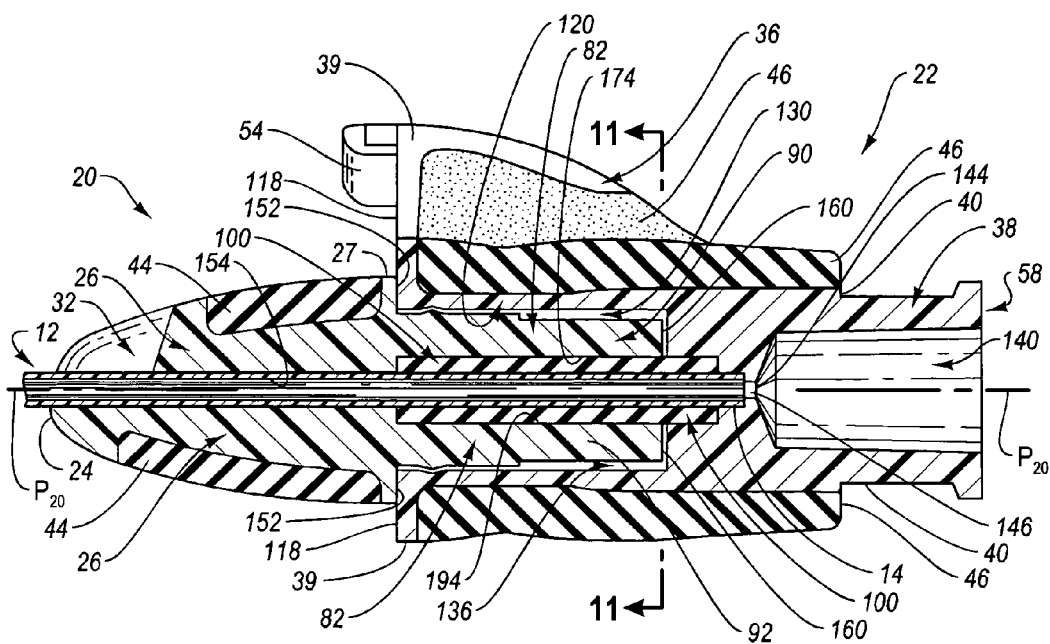
FIG. 10 is a longitudinal cross section of the connection hub of FIG. 1 taken along section line 10-10 therein, thereby illustrating the interaction of internal structures of the elements of the connection hub in the catheter receiving condition thereof.
Figure 11:
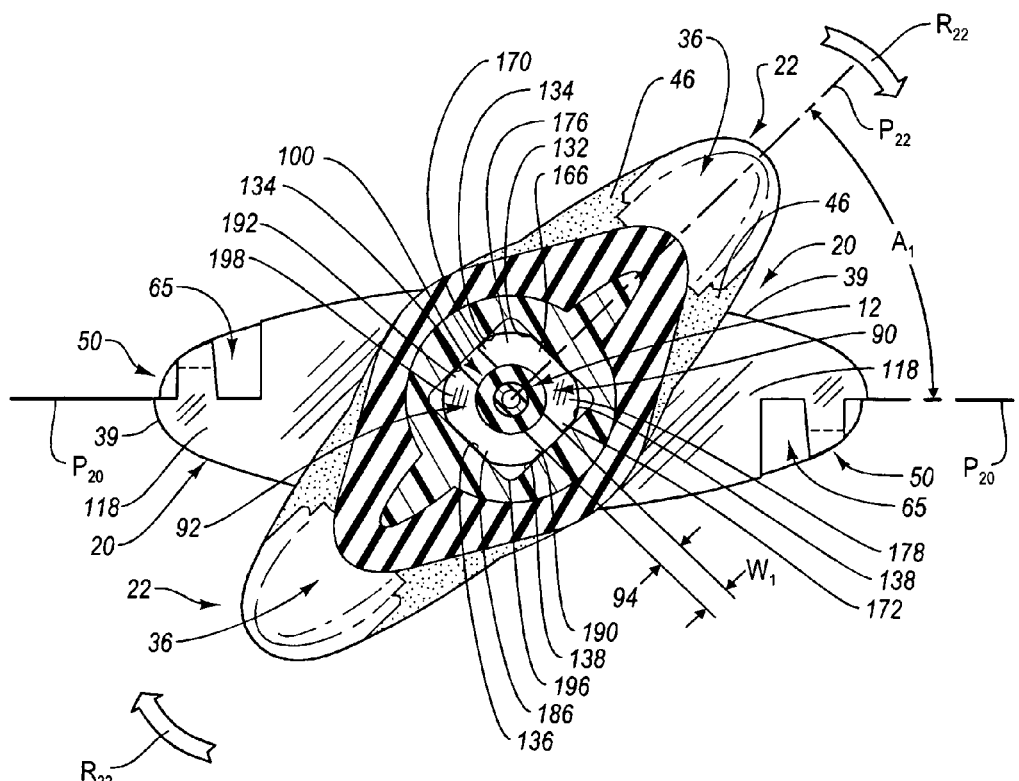
FIG. 11 is a transverse cross section of the connection hub of FIG. 1 taken along section line 11-11 therein at a location more clearly appreciated from the inclusion of section line 11-11 also in FIG. 10.

FIGS. 10 and 11 present cross sections of the elements of connection hub 10 in the catheter receiving condition thereof illustrated in FIG. 1.

In FIG. 10, interface surface 152 at abutment end 127 of actuation handle 26 of catheter receiving element 20 is in engagement with interface surface 118 at abutment end 39 of engagement handle 36 of fluid coupling element 22. First and second clamping jaws 90, 92, with sealing sleeve 100 therebetween are received in clamp actuation socket 130 interior of fluid coupling element 22.

Fluid coupling element 22 is capable of rotation $R_{22}$ relative to catheter receiving element 20 as indicated in FIG. 11 by arrows. Prior to any such rotation, however, plane $P_{22}$ of fluid coupling element 22 is disposed at an acute angle $A_1$ of about 45° relative to plane $P_{20}$ of catheter receiving element 20. Clamping jaws 90, 92 are in an open condition thereof with slot 94 therebetween being of undiminished width $W_1$. Wall 132 of clamp actuation socket 130 opposes outer surface 66 of first clamping jaw 90, and wall 136 of clamp actuation socket 130 opposes outer surface 86 of second clamping jaw 92. Wall 134 of clamp actuation socket 130 opposes side surface 170 of first clamping jaw 90, side surface 192 of second clamping jaw 92, and an entry into slot 94 located therebetween. Wall 138 of clamp actuation socket 130 opposes side surface 172 of first clamping jaw 90, side surface 190 of second clamping jaw 92, and an opening into slot 94 located therebetween.

Figure 11A:
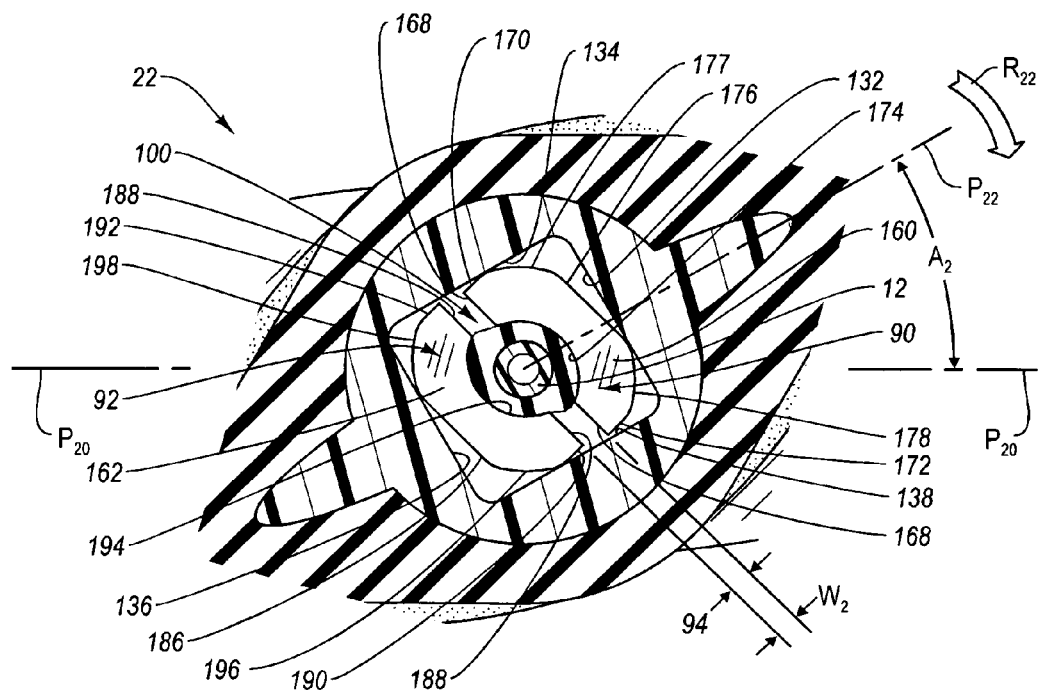
FIGS. 11A and 11B are a sequence of transverse cross sections of internal structures of the catheter receiving condition of the connection hub of FIGS. 10 and 11 undergoing progressively increased relative rotation into the catheter capture condition of the connection hub as illustrated in FIGS. 12 and 13.
Figure 11B:
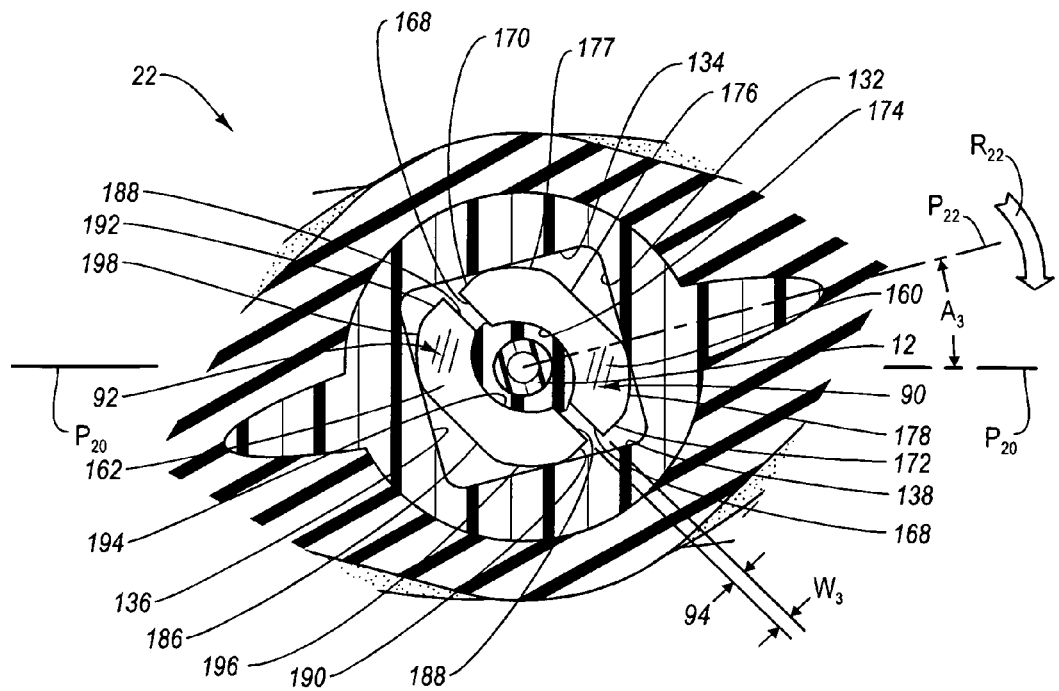

FIGS. 11A and 11B are a sequence of enlarged transverse cross-sectional views of the central portion of FIG. 11 illustrating relative assumed positions by elements of clamp actuation socket 30 and clamping jaws 90, 92, during progressive rotation $R_{22}$ of fluid coupling element 22 relative to catheter receiving element 20.

Plane $P_{20}$ of catheter receiving element 20 is shown in each of FIGS. 11A and 11B, whereby it is to be understood that catheter receiving element 20 and all components thereof, such as clamping jaws 90, 92, remain in the same orientation as shown in FIG. 11, while being an interior feature of fluid coupling element 22, clamp actuation socket 130 engages in coaxial rotation $R_{22}$ relative thereto. The relative rotation of clamp actuation socket 130 illustrated in the sequence of FIGS. 11A and 11B serves to progressively urge first clamping jaw 90 into ever-closer proximity to second clamping jaw 92, compressing sealing sleeve 100 about free end 14 of catheter 12 in the process.

In FIG. 11A, plane $P_{22}$ of fluid coupling element 22 has been caused to engage in rotation $R_{22}$ relative to catheter receiving element 20 from the position illustrated in FIG. 11 by about 15°. As a result, the angle $A_2$ between plane $P_{22}$ of fluid coupling element 22 and plane $P_{20}$ of catheter receiving element 20 is only approximately 30°. Components of catheter receiving element 20, such as clamping jaws 90, 92, as well as sealing sleeve 100 disposed therebetween, remained stationary in that process, but clamp actuation socket 130 rotated approximately 15° relative thereto. As a result, side 134 of actuation socket 130 has commenced to ride over bearing surface 176 on first clamping jaw 90, and side 166 of clamp actuation socket 130 has commenced to ride over bearing surface 178 of first clamping jaw 190. Such relative movement between interior surfaces of clamp actuation socket 130 and the exterior of first clamping jaw 90 is accommodated as a result of planar cross-sectional configuration of first clamping jaw 90 by a radially inward resilient deformation of first clamping jaw 90 toward second clamping jaw 92. Similarly, wall 138 of clamp actuation socket 30 has commenced to ride over bearing surface 96 of second clamping jaw 92, while wall 36 of clamp actuation socket 30 has commenced to ride over bearing surface 98 of second clamping jaw 92. These relative movements between the interior of clamp actuation socket 30 and the exterior of second clamping jaw 92 urge clamping jaw 92 resiliently radially inwardly toward first clamping jaw 90, accommodated in that process by the planar cross-sectional configuration of second clamping jaw 92.

In FIG. 11B, plane $P_{22}$ of fluid coupling element 22 has been caused to engage in rotation $R_{22}$ relative to catheter receiving element 20 from the position illustrated in FIG. 11A by about 15°. As a result, the angle $A_2$ between plane $P_{22}$ of fluid coupling element 22 and plane $P_{20}$ of catheter receiving element 20 is only approximately 30°. Components of catheter receiving element 20, such as clamping jaws 90, 92, as well as sealing sleeve 100 disposed therebetween, remained stationary in that process, but clamp actuation socket 130 rotated approximately another 15° relative thereto. As a result, side 134 of actuation socket 130 has ridden further over bearing surface 176 on first clamping jaw 90, and side 166 of clamp actuation socket 130 has ridden further over bearing surface 178 of first clamping jaw 190. Such relative movement between interior surfaces of clamp actuation socket 130 and the exterior of first clamping jaw 90 is accommodated as a result of planar cross-sectional configuration of first clamping jaw 90 by a radially inward resilient deformation of first clamping jaw 90 toward second clamping jaw 92. Similarly, wall 138 of clamp actuation socket 30 has ridden further over bearing surface 96 of second clamping jaw 92, while wall 36 of clamp actuation socket 30 has ridden further over bearing surface 98 of second clamping jaw 92. These relative movements between the interior of clamp actuation socket 30 and the exterior of second clamping jaw 92 urge clamping jaw 92 resiliently radially inwardly toward first clamping jaw 90, accommodated in that process by the planar cross-sectional configuration of second clamping jaw 92.

Further rotation of fluid coupling element 22 relative to catheter receiving element 20 brings plane $P_{22}$ of fluid coupling element 22 by another 15° into coplanar alignment with plane $P_{20}$ of catheter receiving element 20 in the catheter capture condition of connection hub 10 shown in FIG. 2. The catheter capture condition of connection hub 10 is further illuminated through the cross-sectional views provided in FIGS. 12 and 13.

Figure 13:
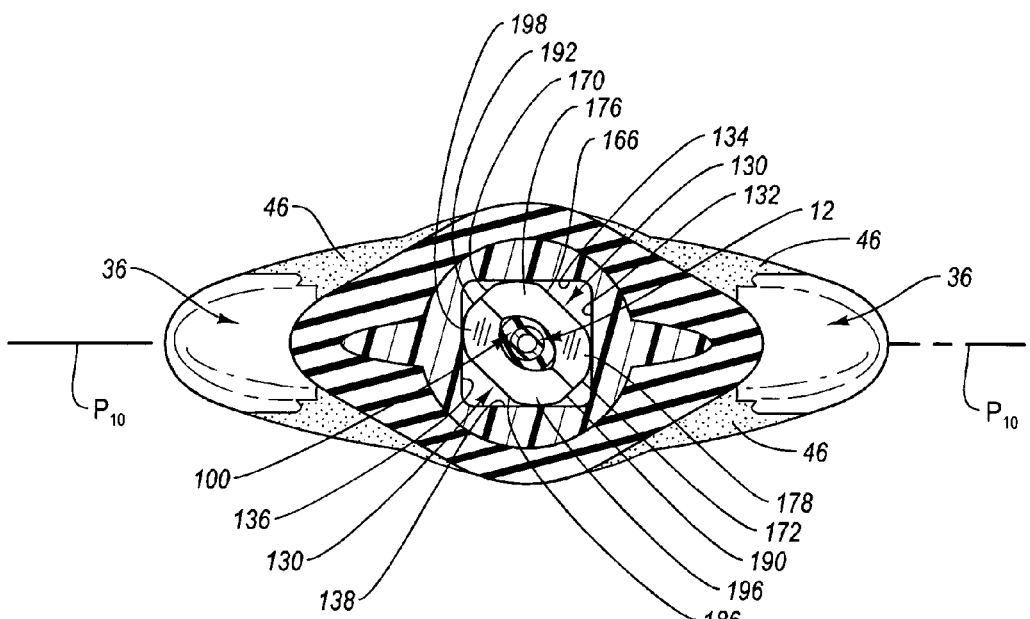
FIG. 13 is a transverse cross section of the connection hub of FIG. 2 taken along section line 11-11 therein at a location more clearly appreciated from the inclusion of section line 13-13 also in FIG. 12.

As seen to best advantage in FIG. 13, the rotation of clamp actuation socket 130 relative to clamping jaws 90, 92 has produced sufficient resilient deformation of clamping jaws 90, 92 radially toward each other as to bring clamping jaws 90, 92 into closed condition thereof. Clamp surface 168 of first clamping jaw 90 abuts clamp surface 188 of second clamping jaw 192. As a result, sealing sleeve 100 is intensely compressed within catheter accommodation recess 174 and catheter accommodation recess 194 that have been brought into aligned opposition by a resilient radially inward deformation of clamping jaws 90, 92. Thus, in the closed condition of clamping jaws 90, 92, free end 14 of catheter 12 is gripped mechanically through sealing sleeve 100 by catheter accommodation recesses 174, 194, and sealing sleeve 100 is urged by clamping jaws 90, 92, into a fluid seal about the exterior of free end 14 of catheter 12.

Figure 12:
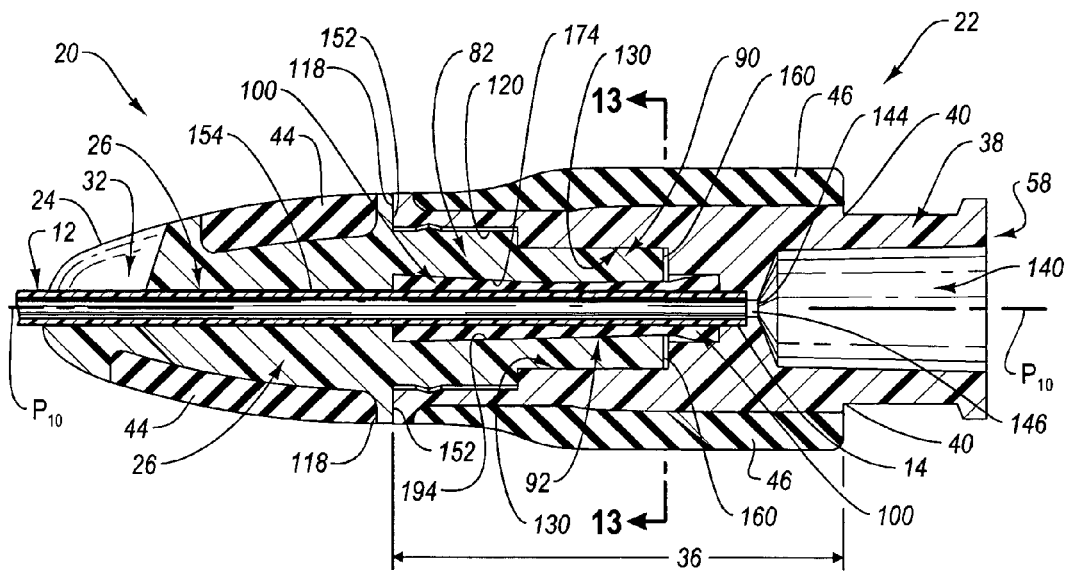
FIG. 12 is a longitudinal cross section of the connection hub of FIG. 2 taken along section line 12-12 therein, thereby illustrating the interaction of internal structures of the elements of the connection hub in the catheter capture condition thereof.

As seen to best advantage in FIG. 12, the force exerted on the exterior of free end 14 of catheter 12 by clamping jaws 90, 92, is focused longitudinally along catheter tube 12 at a location between first clamp tip 160 of first clamping jaw 90 and second clamp tip 162 of second clamping jaw 192. The force of the mechanical grip exercised on catheter 12 in this manner is thus advantageously controllable through the design of clamp actuation socket 30 and the cross-sectional configurations of clamping jaws 90, 92.

FIGS. 14A, 14B, 15A, and 15B are alternate embodiments of FIGS. 11A and 11B and are a sequence of enlarged transverse cross-sectional views of the central portion of FIG. 11 illustrating relative assumed positions by elements of clamp actuation socket 30 and clamping jaws 90, 92, during progressive rotation $R_{22}$ of fluid coupling element 22 relative to catheter receiving element 20.

Plane $P_{20}$ of catheter receiving element 20 is shown in each of FIGS. 11A and 11B, whereby it is to be understood that catheter receiving element 20 and all components thereof, such as clamping jaws 90, 92, remain in the same orientation as shown in FIG. 11, while being an interior feature of fluid coupling element 22 clamp actuation socket 130 engages in coaxial rotation $R_{22}$ relative thereto. The relative rotation of clamp actuation socket 130 illustrated in the sequence of FIGS. 11A and 11B serves to progressively urge first clamping jaw 90 into ever closer proximity to second clamping jaw 92, compressing sealing sleeve 100 about free end 14 of catheter 12 in the process.

In FIG. 11A, plane $P_{22}$ of fluid coupling element 22 has been caused to engage in rotation $R_{22}$ relative to catheter receiving element 20 from the position illustrated in FIG. 11 by about 15°. As a result, the angle $A_2$ between plane $P_{22}$ of fluid coupling element 22 and plane $P_{20}$ of catheter receiving element 20 is only approximately 30°. Components of catheter receiving element 20, such as clamping jaws 90, 92, as well as sealing sleeve 100 disposed therebetween, remained stationary in that process, but clamp actuation socket 130 rotated approximately 15° relative thereto. As a result, side 134 of actuation socket 130 has commenced to ride over bearing surface 176 on first clamping jaw 90, and side 166 of clamp actuation socket 130 has commenced to ride over bearing surface 178 of first clamping jaw 190. Such relative movement between interior surfaces of clamp actuation socket 130 and the exterior of first clamping jaw 90 is accommodated as a result of planar cross-sectional configuration of first clamping jaw 90 by a radially inward resilient deformation of first clamping jaw 90 toward second clamping jaw 92. Similarly, wall 138 of clamp actuation socket 30 has commenced to ride over bearing surface 96 of second clamping jaw 92, while wall 36 of clamp actuation socket 30 has commenced to ride over bearing surface 98 of second clamping jaw 92. These relative movements between the interior of clamp actuation socket 30 and the exterior of second clamping jaw 92 urge clamping jaw 92 resiliently radially inwardly toward first clamping jaw 90, accommodated in that process by the planar cross-sectional configuration of second clamping jaw 92.

In FIG. 11B, plane $P_{22}$ of fluid coupling element 22 has been caused to engage in rotation $R_{22}$ relative to catheter receiving element 20 from the position illustrated in FIG. 11A by about 15°. As a result, the angle $A_2$ between plane $P_{22}$ of fluid coupling element 22 and plane $P_{20}$ of catheter receiving element 20 is only approximately 30°. Components of catheter receiving element 20, such as clamping jaws 90, 92, as well as sealing sleeve 100 disposed therebetween, remained stationary in that process, but clamp actuation socket 130 rotated approximately another 15° relative thereto. As a result, side 134 of actuation socket 130 has ridden further over bearing surface 176 on first clamping jaw 90, and side 166 of clamp actuation socket 130 has ridden further over bearing surface 178 of first clamping jaw 190. Such relative movement between interior surfaces of clamp actuation socket 130 and the exterior of first clamping jaw 90 is accommodated as a result of planar cross-sectional configuration of first clamping jaw 90 by a radially inward resilient deformation of first clamping jaw 90 toward second clamping jaw 92. Similarly, wall 138 of clamp actuation socket 30 has ridden further over bearing surface 96 of second clamping jaw 92, while wall 36 of clamp actuation socket 30 has ridden further over bearing surface 98 of second clamping jaw 92. These relative movements between the interior of clamp actuation socket 30 and the exterior of second clamping jaw 92 urge clamping jaw 92 resiliently radially inwardly toward first clamping jaw 90, accommodated in that process by the planar cross-sectional configuration of second clamping jaw 92.

Further rotation of fluid coupling element 22 relative to catheter receiving element 20 brings plane $P_{22}$ of fluid coupling element 22 by another 15° into coplanar alignment with plane $P_{20}$ of catheter receiving element 20 in the catheter capture condition of connection hub 10 shown in FIG. 2. The catheter capture condition of connection hub 10 is further illuminated through the cross-sectional views provided in FIGS. 12 and 13.

As seen to best advantage in FIG. 13, the rotation of clamp actuation socket 130 relative to clamping jaws 90, 92 has produced sufficient resilient deformation of clamping jaws 90, 92 radially toward each other as to bring clamping jaws 90, 92 into closed condition thereof. Clamp surface 168 of first clamping jaw 90 abuts clamp surface 188 of second clamping jaw 192. As a result, sealing sleeve 100 is intensely compressed within catheter accommodation recess 174 and catheter accommodation recess 194 that have been brought into aligned opposition by a resilient radially inward deformation of clamping jaws 90, 92. Thus, in the closed condition of clamping jaws 90, 92, free end 14 of catheter 12 is gripped mechanically through sealing sleeve 100 by catheter accommodation recesses 174, 194, and sealing sleeve 100 is urged by clamping jaws 90, 92, into a fluid seal about the exterior of free end 14 of catheter 12.

As seen to best advantage in FIG. 12, the force exerted on the exterior of free end 14 of catheter 12 by clamping jaws 90, 92, is focused longitudinally along catheter tube 12 at a location between first clamp tip 160 of first clamping jaw 90 and second clamp tip 162 of second clamping jaw 192. The force of the mechanical grip exercised on catheter 12 in this manner is thus advantageously controllable through the design of clamp actuation socket 30 and the cross-sectional configurations of clamping jaws 90, 92.

Figure 14A:
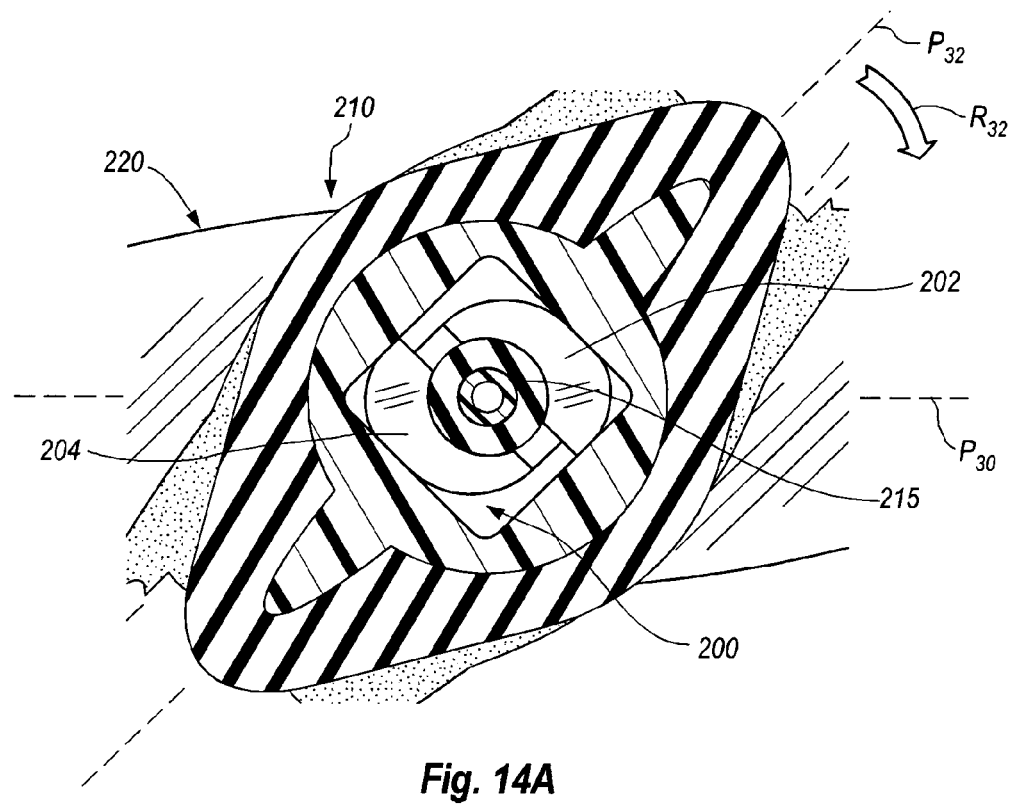
FIGS. 14A and 14B are a sequence of transverse cross sections of internal structures of an embodiment of a catheter receiving condition of an alternate embodiment of a connection hub undergoing progressively increased relative rotation into the catheter capture condition of the connection hub.
Figure 14B:
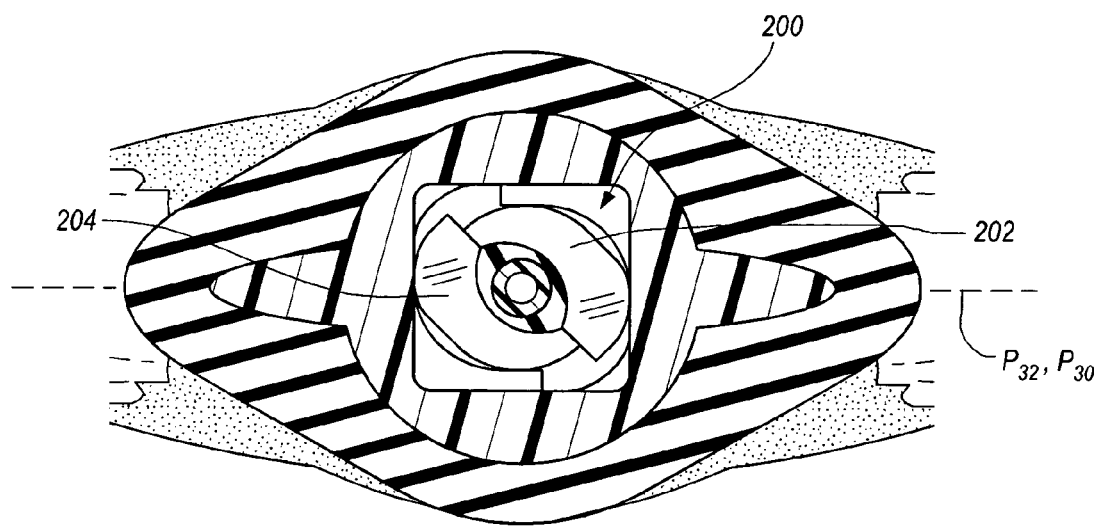
Figure 15A:
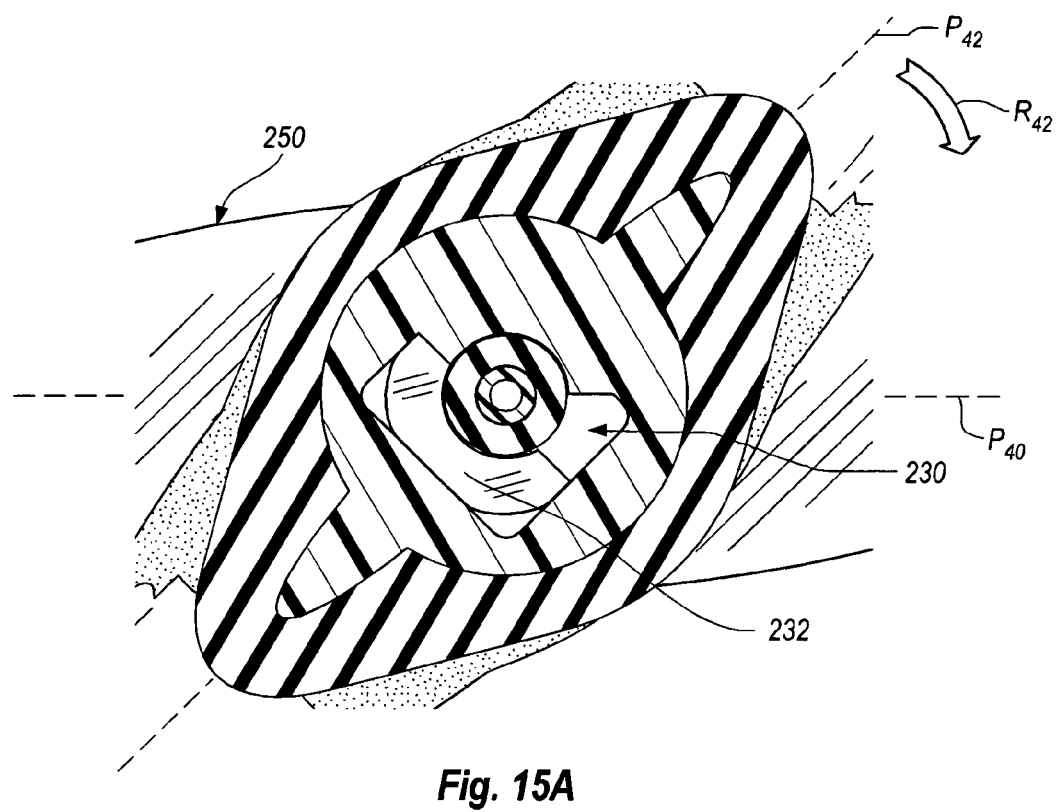
FIGS. 15A and 15B are a sequence of transverse cross sections of internal structures of an embodiment of a catheter receiving condition of an alternate embodiment of a connection hub undergoing progressively increased relative rotation into the catheter capture condition of the connection hub.
Figure 15B:
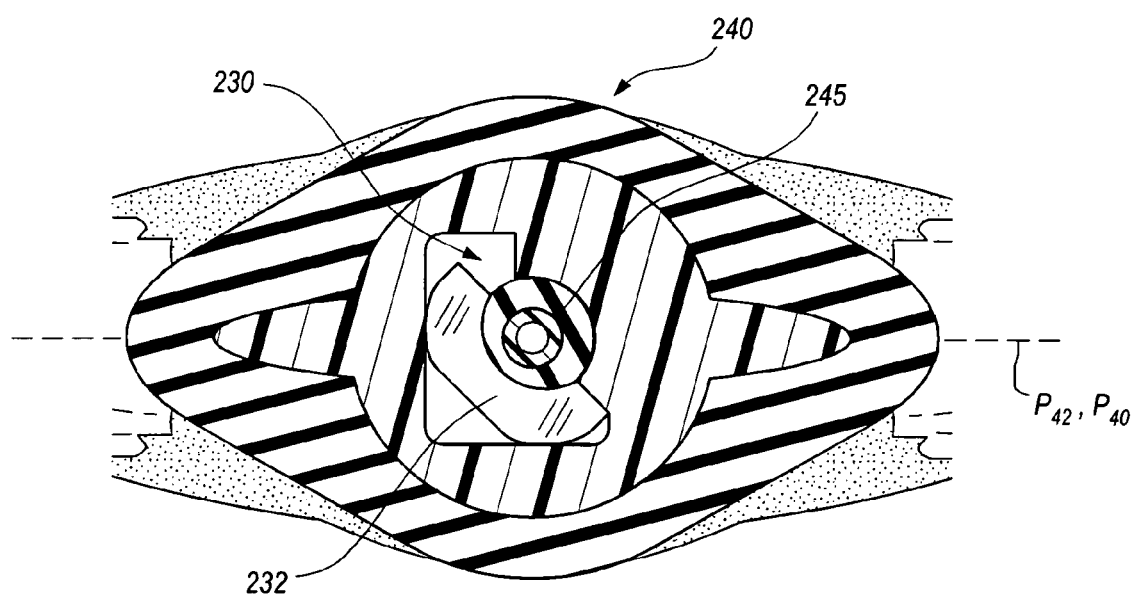

As can be seen in FIGS. 14A, 14B, 15A, and 15B, embodiments of the present invention contemplate various configurations of clamp actuation sockets and clamp actuation jaws. Referring to FIGS. 14A and 14B, a configuration of a clamp actuation socket 200 and clamping jaws 202, 204 is illustrated. In general, FIGS. 14A and 14B illustrate an actuation socket 200 that does not have four flat side surfaces. In general, FIGS. 15A and 15B illustrate a configuration of an actuation socket 230 and a single clamping jaw 232.

In FIG. 14A, plane $P_{32}$ of fluid coupling element 210 has been caused to engage in rotation $R_{32}$ relative to catheter receiving element 220. Components of catheter receiving element 220, such as clamping jaws 202, 204, as well as sealing sleeve 215 disposed therebetween, remain stationary during a rotation, but clamp actuation socket 200 rotates relative thereto. These relative movements between the interior of clamp actuation socket 200 and clamping jaw 202 and clamping jaw 204 urge clamping jaw 202 and clamping jaw 204 radially toward one another.

As can be best seen from FIG. 14B, the uneven sides of actuation socket 200 substantially prevent clamping jaw 202 and clamping jaw 204 from rotating and/or twisting.

In FIG. 14B, plane $P_{22}$ of fluid coupling element 210 has been caused to engage in rotation $R_{32}$ relative to catheter receiving element 220 from the position illustrated in FIG. 14A by about 45°. As a result, the angle between plane $P_{22}$ of fluid coupling element 210 and plane $P_{30}$ of catheter receiving element 220 is only approximately 0°, about coplanar alignment.

Coplanar alignment with plane $P_{30}$ of catheter receiving element 220 is the catheter capture condition of a connection hub.

In FIG. 15A, plane $P_{42}$ of fluid coupling element 240 has been caused to engage in rotation $R_{42}$ relative to catheter receiving element 250. Components of catheter receiving element 250, such as clamping jaw 232, as well as sealing sleeve 245 disposed therebetween, remain stationary during a rotation, but clamp actuation socket 230 rotates relative thereto. These relative movements between the interior of clamp actuation socket 200 and clamping jaw 232 urges clamping jaw 232 radially toward and about sealing sleeve 245.

As can be best seen from FIG. 15B, rotation of fluid coupling element 240 relative to clamping jaw 232 through actuation socket 230 urges clamping jaw 232 into or toward sealing sleeve 245. In various embodiments, actuation socket 230 is shaped or formed such that actuation socket 230 resists clamping jaw 232 from rotating and/or twisting. In various other embodiments, a clamping jaw or jaws is shaped or formed such the clamping jaw or jaws resists rotation or twisting.

In FIG. 15B, plane $P_{42}$ of fluid coupling element 240 has been caused to engage in rotation $R_{42}$ relative to catheter receiving element 250 from the position illustrated in FIG. 15A by about 45°. As a result, an angle between plane $P_{42}$ of fluid coupling element 240 and plane $P_{40}$ of catheter receiving element 250 is only approximately 0°, about coplanar alignment.

Coplanar alignment with plane $P_{40}$ of catheter receiving element 250 is the catheter capture condition of a connection hub.

Figure 16:
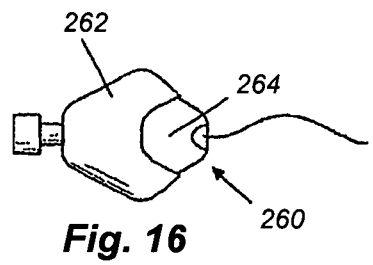
FIG. 16 is an illustration of a perspective view of an embodiment of a connection hub comprising a fluid coupling element angular portion shielding a catheter receiving element.
Figure 17:
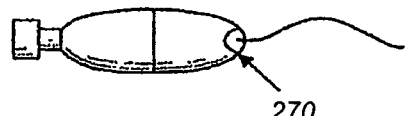
FIG. 17 is an illustration of a perspective view of an embodiment of an elliptical connection hub comprising a fluid coupling element and a catheter receiving element.
Figure 18:
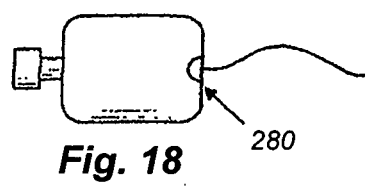
FIG. 18 is an illustration of a perspective view of an embodiment of a square connection hub comprising a fluid coupling element and a catheter receiving element.
Figure 19:
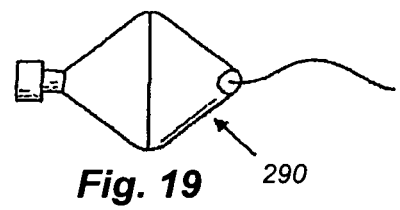
FIG. 19 is an illustration of a perspective view of an embodiment of a diamond connection hub comprising a fluid coupling element and a catheter receiving element.
Figure 20:
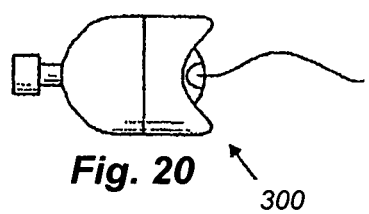
FIG. 20 is an illustration of a perspective view of an embodiment of an arcuate connection hub comprising a fluid coupling element and a catheter receiving element.
Figure 21A:
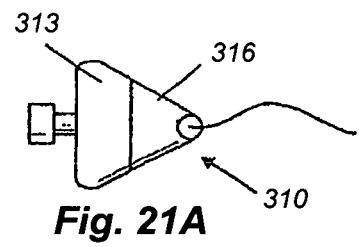
FIGS. 21A and 21B are illustrations of perspective views of embodiments of a triangular connection hub comprising a fluid coupling element and a catheter receiving element; and, FIGS. 22A and 22B are illustrations of perspective views of an embodiment of a connection hub comprising a fluid coupling element and a catheter receiving element wherein a cap is extending at an angle from the embodiment of the connection hub.
Figure 21B:
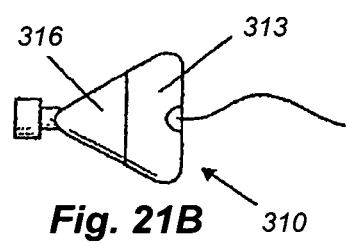
Figure 22A:
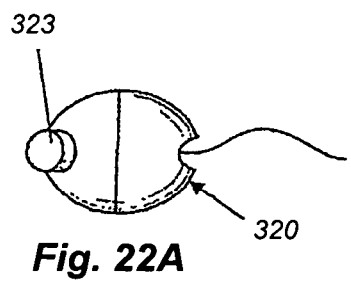
Figure 22B:
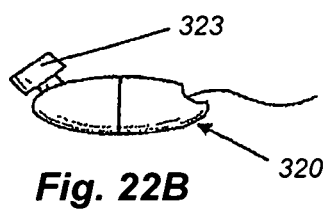

Further embodiments of the present invention are disclosed in FIGS. 16-22. In general, FIGS. 16-22 are included within this specification as an illustration that the scope of the appended claims is not limited. FIG. 16 is an illustration of a perspective view of an embodiment of a connection hub 260 comprising a fluid coupling element angular portion 262 shielding a catheter receiving element 264. FIG. 17 is an illustration of a perspective view of an embodiment of an elliptical connection hub 270 comprising a fluid coupling element and a catheter receiving element. FIG. 18 is an illustration of a perspective view of an embodiment of a quadrangular connection hub 280 comprising a fluid coupling element and a catheter receiving element. FIG. 19 is an illustration of a perspective view of an embodiment of a diamond connection hub 290 comprising a fluid coupling element and a catheter receiving element. FIG. 20 is an illustration of a perspective view of an embodiment of an arcuate connection hub 300 comprising a fluid coupling element and a catheter receiving element. FIG. 21A is an illustration of a perspective view of an embodiment of a triangular connection hub 310 comprising a fluid coupling element 313 and a catheter receiving element 316. FIG. 21B is an illustration of a perspective view of an embodiment of a triangular connection hub 310 comprising a fluid coupling element 316 and a catheter receiving element 313. FIGS. 22A and 22B are illustrations of perspective views of an embodiment of a connection hub 320 comprising a fluid coupling element and a catheter receiving element wherein a cap 323 is extending at an angle from the embodiment of the connection hub.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A connection hub, comprising:
    a first component comprising a funnel-shaped, open-topped guideway recessed in the outer first component for receiving a portion of a catheter; and
    a second component attached and rotatable relative to the first component to secure the portion of the catheter at least partially received within the first component and the second component, wherein, in a catheter capture condition of the connection hub, the combination of the exterior of the first component and the exterior of the second component of the connection hub form a circular disk, and wherein a planar interface surface of the first component is configured to be contiguous with at least a portion of a complementary planar interface surface of the second component during rotation of the connection hub between the catheter capture condition and a catheter receiving condition.

2. The connection hub of claim 1, wherein, in the catheter capture condition, an actuation portion of the connection hub is configured to radially urge at least one clamping jaw of the connection hub radially inward toward the portion of the catheter received within the first component.

3. The connection hub of claim 2, wherein:
    the at least one clamping jaw comprises a pair of clamping jaws;
    the connection hub further comprises a compressible sealing sleeve retained between the pair of clamping jaws and configured to receive a portion of the catheter; and
    in the catheter capture condition, the actuation portion of the connection hub is configured to radially urge each of the pair of clamping jaws radially inward to compress the compressible sealing sleeve.

4. The connection hub of claim 3, wherein the first component comprises the pair of clamping jaws extending from a planar interface surface of the first component.

5. The connection hub of claim 4, wherein the second component comprises an opening configured to receive the pair of clamping jaws of the first component.

6. The connection hub of claim 5, wherein the opening of the second component comprises an actuation socket having a substantially square cross section configured to radially urge the pair of clamping jaws of the first component radially inward toward the portion of the catheter received within the first component.

7. The connection hub of claim 1, wherein the open-topped guideway comprises a wedge-shaped floor positioned adjacent to an opening for receiving the portion of the catheter.

8. The connection hub of claim 1, wherein, in the catheter capture condition, the connection hub comprises a generally planar structure.

9. The connection hub of claim 1, wherein the first component and the second component each comprise cooperating latching elements, the latching elements interacting in the catheter capture condition of the connection hub to resist rotation of the first component relative to the second component out of the catheter capture condition.

10. A connection hub, comprising:
    a receiving body comprising at least one clamping jaw and configured to slidably admit a portion of a catheter into the connection hub, the exterior of the receiving body comprising a first actuation handle;
    a compressible sealing sleeve disposed in the connection hub; and
    a fluid coupling element configured for coupling to a fluid source, the fluid coupling element comprising a connector configured to couple the connection hub to a fluid source, the fluid coupling element rotatably secured to the receiving body for movement relative thereto into and out of a catheter capture condition of the connection hub, the exterior of the fluid coupling element comprising a second actuation handle having a planar interface surface configured to be contiguous with at least a portion of a complementary planar interface surface of the first actuation handle when the connection hub is moved into and out of the catheter capture condition, the second actuation handle useable in cooperation with the first actuation handle to move the fluid coupling element relative to the receiving body into and out of the catheter capture condition of the connection hub, wherein, in the catheter capture condition, a portion of the fluid coupling element is configured to radially urge the at least one clamping jaw radially inward toward the compressible sealing sleeve, wherein the first actuation handle and the second actuation handle are in alignment with one another when the fluid coupling element and the receiving body are in the catheter capture condition of the connection hub, wherein the first actuation handle and the second actuation handle are rotationally offset when the fluid coupling element and the receiving body are out of the catheter capture condition of the connection hub.

11. The connection hub of claim 10, wherein:
    the at least one clamping jaw comprises a pair of clamping jaws; and
    in the catheter capture condition, the portion of the fluid coupling element is configured to radially urge each of the pair of clamping jaws radially inward to compress the compressible sealing sleeve.

12. The connection hub of claim 11, wherein the pair of clamping jaws extends from a planar interface surface of the receiving body, and wherein the fluid coupling element comprises an opening configured to receive the pair of clamping jaws.

13. The connection hub of claim 10, wherein:
    the surface of the first actuation handle comprises an inlay of skin-compatible material; and
    the surface of the second actuation handle comprises an inlay of skin-compatible material.

14. The connection hub of claim 10, wherein the receiving body and the fluid coupling element bear, respectively, cooperating latching elements, the latching elements interacting in the catheter capture condition of the connection hub to resist rotation of the fluid coupling element relative to the receiving body out of the catheter capture condition.

15. The connection hub of claim 10, wherein in the catheter capture condition, the connection hub comprises a generally planar structure.

16. A connection hub, comprising:
    a first component comprising a funnel-shaped, open-topped guideway recessed in the outer first component leading to an access opening for receiving a portion of a catheter and a first actuation handle configured as a first semicircular disk, the funnel-shaped, open-topped guideway comprising a depression formed in the first component at a front portion and at a top portion of the first component such that the open-topped guideway is accessible and viewable from both the front portion and the top portion of the first component, the open-topped guideway having a wedge-shaped floor recessed in the first component with respect to the surrounding exterior of the first component, the wedge-shaped floor leading to and terminating at the access opening; and a second component attached and rotatable relative to the first component, the second component comprising a second actuation handle having a portion configured as a second semicircular disk of diameter and thickness equal to the diameter and thickness of the first semicircular disk, wherein, in a catheter capture condition of the connection hub, the combination of the exterior of the first component and the exterior of the second component of the connection hub form a portion of a circular disk.

17. The connection hub of claim 16, wherein:

the periphery of the first semicircular disk and the periphery of the second semicircular disk include a linear, diametrical edge; and the linear, diametrical edge of the periphery of the first semicircular disk is rotatably abutted to the linear diametrical edge of the second semicircular disk.

18. A connection hub, comprising:

a receiving body comprising at least one clamping jaw and configured to slidably admit a portion of a catheter into the connection hub, the exterior of the receiving body comprising a first actuation handle configured as a first semicircular disk;

a compressible sealing sleeve disposed in the connection hub; and a fluid coupling element comprising a connector configured to couple the connection hub to a fluid source, the fluid coupling element rotatably secured to the receiving body for movement relative thereto into and out of a catheter capture condition of the connection hub, the exterior of the fluid coupling element comprising a second actuation handle configured as at least a portion of a second semicircular disk of diameter and thickness equal to the diameter and thickness of the first semicircular disk and useable in cooperation with the first actuation handle to move the fluid coupling element relative to the receiving body into and out of the catheter capture condition of the connection hub, wherein, in the catheter capture condition, a portion of the fluid coupling element is configured to radially urge the at least one clamping jaw radially inward toward the compressible sealing sleeve, and wherein a planar interface surface of the receiving body is configured to be contiguous with at least a portion of a complementary planar interface surface of the fluid coupling element during rotation of the connection hub between the catheter capture condition and a catheter receiving condition.

19. The connection hub of claim 18, wherein:

the periphery of the first semicircular disk and the periphery of the second semicircular disk include a linear, diametrical edge; and the linear, diametrical edge of the periphery of the first semicircular disk is rotatably abutted to the linear diametrical edge of the second semicircular disk.

* * * * *